United States Patent [19]

Utyamyshev et al.

[11] Patent Number: 4,505,272

[45] Date of Patent: Mar. 19, 1985

[54] SURGICAL SUTURING INSTRUMENT FOR PERFORMING ANASTOMOSES BETWEEN STRUCTURES OF THE DIGESTIVE TRACT

[75] Inventors: Rustam I. Utyamyshev, Boris A. Smirnov, Nikolai N. Kanshin, Ivan A. Korolkov, Tatyana L. Ivanova, all of Moscow, U.S.S.R.

[73] Assignee: Vsesojuzny Nauchno-Issledovatelsky i Ispytatelny Institut Meditsinskoi Tekhniki, Moscow, U.S.S.R.

[21] Appl. No.: 468,484

[22] Filed: Feb. 22, 1983

[30] Foreign Application Priority Data

Feb. 23, 1982 [SU] U.S.S.R. ............................ 3400255

[51] Int. Cl.³ .............................................. A61B 17/11
[52] U.S. Cl. .................................. 128/305; 128/334 R; 128/334 C; 227/19; 227/155; 227/DIG. 1
[58] Field of Search ............... 128/334 R, 334 C, 305; 227/DIG. 1, 19, 155

[56] References Cited

U.S. PATENT DOCUMENTS 3,552,626  1/1971  Astaflev et al. ............ 227/DIG. 1 X Primary Examiner—Michael H. Thaler
Attorney, Agent, or Firm—Fleit, Jacobson, Cohn & Price

[57] ABSTRACT

An instrument comprising a tubular staple case is disclosed, the case being traversed by a supporting rod extending outwardly therefrom with its front end. The tubular case is used to mount a plunger with a knife arranged on the rod. An abutment head mounted on the front end of the rod is made generally longitudinally detachable consisting of two members, an internal member detachably mounted on the front end of the rod and an external member encompassing the internal member and made up of interdetachable rests. Moreover, provision is made for a staple magazine and a female die with grooves for bending staples as well as a drive imparting motion to the plunger and a mechanism for adjusting the gap between an end of the case and an end of the head.

6 Claims, 4 Drawing Figures

SURGICAL SUTURING INSTRUMENT FOR PERFORMING ANASTOMOSES BETWEEN STRUCTURES OF THE DIGESTIVE TRACT

FIELD OF THE INVENTION

This invention pertains to medical engineering, and more specifically to a surgical instrument for performing anastomoses between structures of the digestive tract.

THE PRIOR ART

The prior art affords the example of a suturing instrument for performing anastomoses between the organs of the digestive tract comprising a tubular staple case with a supporting rod passing through said tubular case and extending outwardly therefrom with its front end, a plunger with a knife arranged coaxially within the tubular case, mounted on said rod movably with respect to its front end, an abutment head with a supporting washer for the knife, mounted on the front end of the rod, a staple magazine arranged coaxially within the tubular case and a female die for bending staples, said female die being mounted on said head, and a drive imparting motion to the plunger with the knife and a means for adjusting the gap between an end of the case and an end of the head.

The working part of the abutment head is fashioned into a cylindrical body whose end portion is provided with a plurality of circumferentially arranged grooves for bending the staples, an aperture adapted to accomodate the supporting washer for the knife and another aperture adapted to receive the knife.

The abutment head is secured to the front end of the rod by means of a special nut.

The staple magazine is made up of a series of staple grooves disposed along the circumference of the tubular staple case and opening into its end portion to face the grooves for bending the staples.

The number and arrangement of the staple grooves are in accordance with the number and arrangement of the grooves for bending the staples. Each staple groove accomodates one C-shaped metal staple with sharpened shanks.

The working part of the plunger consists of a hollow cylinder divided into a number of flaps. The number and arrangement of the flaps of the plunger corresponds to the number and arrangement of the staple grooves of the magazine, each flap of the plunger in initial position partially extending into a staple groove of the magazine. The inside of the plunger's cylindrical portion is used to install the knife for incising tissue, while the cylindrical portion is in turn secured to a hollow rod movably mounted on the supporting rod to allow reciprocating movement along the staple case of the instrument.

The gap adjusting means (designated as the suturing gap between the end of the case and the end of the head) comprises a nut connected threadedly to the stem of the supporting rod. The nut is attached movably to the case which permits rotation about its longitudinal axis.

The instrument is provided with a rigidly fixed handle anchored to the case and a movable handle hinged to said case. A return spring is placed between the movable and stationary handles. The drive imparting motion to the plunger with the knife is essentially a movable handle engaging in a movable pair the groove of plunger stem.

The instrument is provided with compression rings made substantially from silicone rubber and mounted on the abutment head and staple case.

The instrument is operated in the following manner.

Prior to surgery the staple magazine is loaded with P-shaped metal staples, i.e. one staple is inserted into each magazine groove in such a way that its sharpened shanks face toward the abutment head. The supporting washer is positioned into the abutment head aperture whereupon the compression rings are mounted on the abutment head and the staple case. Being thus assembled the instrument is subjected to sterilization and then transported to the operating theatre.

In the course of surgery the working part of the instrument is introduced into the tubular structure to be sutured (for example, such natural body opening as the human anus).

Rotation of the gap adjusting means nut counterclockwise causes the abutment head to move away from the staple case. Ends of the sutured tubular structure are joined by a purse-string suture commonly used in surgery. One end is tied around the abutment head on the supporting rod, while the other end envelops the tubular staple case on the supporting rod. Subsequent rotation of the nut of the gap adjusting means clockwise brings the abutment head toward the staple case to form a suturing gap (the gap between the ends of the case and the head usually selected to produce tight tissue coaptation avoiding tension with regularly bent C-shaped metal staples).

Pressure exerted on the movable handle urges the plunger with the knife to slide through the stem in the general direction of the abutment head. Simultaneously, the plunger flaps push the C-shaped metal staples out of the staple grooves. The staples, after piercing the compression rings and tissue to be sutured with their sharpened shanks, stop against the staple bending grooves and are bent in the shape of "B" securely joining the tissue to the compression rings. At the same time the knife incises the tissue on an elastic base thereby producing the desired anastomosis. Since in incising the knife penetrates into the elastic base, reliability of the maneuver is increased.

The making and suturing of the anastomosis is thus completed. After the final stage of suturing is over, counterclockwise rotation of the gap adjusting means nut causes the abutment head to move away from the staple case so that the instrument can be withdrawn from the tubular structure.

A drawback of the known instrument resides in the complicated procedure of withdrawing the abutment head through the anastomotic opening following completion of the suturing since the diameter of the opening excised with the knife must naturally be smaller than that of the circular staple suture skirting the opening, and the latter diameter must in turn be smaller than the outer diameter of the abutment head. The abutment head is particularly difficult to deliver through anastomoses formed with compression rings. This gives rise to additional trauma of the structure at the site of the anastomosis.

SUMMARY OF THE INVENTION

It is an object of this invention to provide a surgical suturing instrument for performing anastomoses between structures of the digestive tract which would ensure atraumatic withdrawal of the instrument in any type of anastomosis-staple (single-stitch, double-stitch, etc) or compression.

Another object of this invention is to provide an instrument of the type referred to above which would ensure a range of anastomotic procedures of the staple and compression variety.

A still further important object is to provide a surgical suturing instrument for performing anastomoses between structures of the digestive tract which would ensure a hermetic and hemostatic suture.

Among others an important object is to provide a surgical suturing instrument for performing anastomoses between the structures of the digestive tract which would reduce the postoperative incompetence in sutures.

The objects already referred to and others are accomplished due to the fact that in a surgical suturing instrument for performing anastomoses between structures of the digestive tract comprising a tubular staple case with a supporting rod passing through said tubular case and extending outwardly therefrom with its front end, a plunger with a knife arranged coaxially within the tubular case, mounted on said rod movably with respect to its front end, an abutment head with a supporting washer for the knife, mounted on the front end of the rod, a stapling magazine arranged coaxially within the tubular case and a female die for bending staples, said female die being mounted on said head, and a drive imparting motion to the plunger with the knife and a means for adjusting the gap between the ends of the case and the head, according to the invention, the head is made axially detachable consisting of two members, an internal detachable member mounted on the front end of the rod, and an external member encompassing the internal member and made up of interdetachable rests, as well as by dint of a means of interlocking the internal member and the rests of the external member along the surface of their engagement against the radial displacement of the rests of the external member.

The advantage of this instrument resides in the unique design of the abutment head which ensures atraumatic withdrawal of the instrument following completion of the anastomotic procedure for a variety of anastomoses, for example, staple and compression, as well as good hermetic and hemostatic characteristics of the resultant suture and reduced postoperative incompetence in sutures.

Other embodiments of the abutment head are possible, for example, the abutment head can be made without the internal member and comprise solely an external member encompassing the front end of the supporting rod and formed by interchangeable parts, while incorporating a means of interlocking one front end of the supporting rod and the parts of the external member along the surface of their engagement against the radial displacement of the parts of the external member.

It is expedient that stapling be effected by means of key grooves made in the body of the internal member and keys engaging said grooves, said keys being formed on the rests of the external member.

It is preferable that the supporting rod be furnished with a longitudinal groove made in between the front end and the staple case, said groove adapted to accomodate a flat spring, one end whereof is rigidly joined to the plunger, while its other free end is provided with a tooth, and one of the rests of the external member is provided with a mating projection adapted to engage said tooth in such a manner that a meshed pair formed by the tooth and the mating projection permits axial movement of the rests.

It is preferred that provision be made for a means temporarily connecting the detachable rests together.

It is expedient that the detachable rests be provided with lugs, and the internal member be provided with an opening for passing a ligature to maintain the rests of the external member and the instrument in interlocked position upon dismantling the abutment head.

It is likewise preferred that the end surface of the staple case and the end surface of the head lying mutually in opposition be used to loosely mount compression rings.

BRIEF DESCRIPTION OF THE DRAWINGS

Hereinafter the invention is described by way of concrete, and yet in no wise limiting, embodiments thereof taken in conjunction with the accompanying drawings in which.

DETAILED DESCRIPTION OF PREFERRED EMBODIMENT

Figure 1:
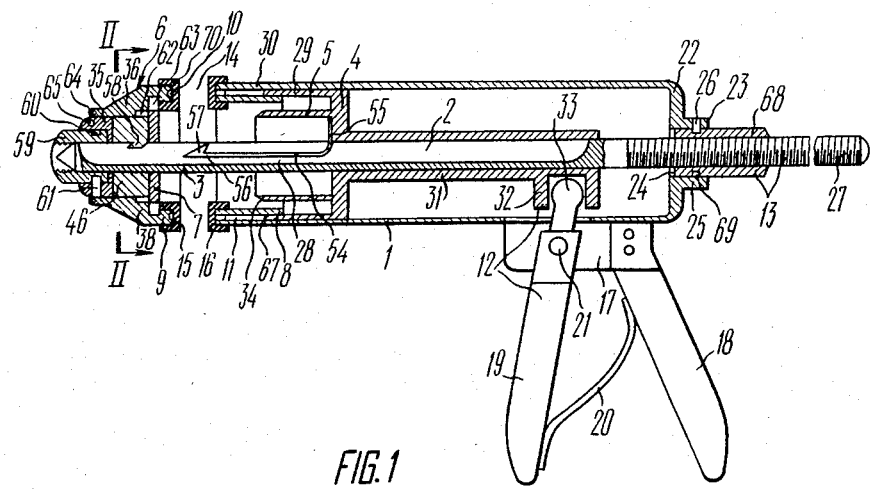
FIG. 1 is a general fragmentary longitudinally sectional view of the surgical suturing instrument for performing anastomoses between structures of the digestive tract.

In this description identical parts in drawings are designated by the same reference numerals.

The surgical suturing instrument for performing anastomoses between structures of the digestive tract (FIG. 1) comprises a tubular staple case I with a supporting rod 2 passing through said tubular case I and extending outwardly therefrom with its front end 3, a plunger 4 with a knife 5 arranged coaxially within the tubular case, mounted on said rod 2 movably with respect to its front end 3, an abutment head 6 with a supporting washer 7 for the knife 5 mounted on the front end 3 of the rod 2, a staple magazine 8 arranged coaxially within the tubular case I and a female die 9 with grooves 10 for bending staples II, said female die being mounted on said head 6, and a drive 12 imparting motion to the plunger 4 with the knife 5 and a means 13 for adjusting the gap 14 between an end 13 of the case I and an end 16 of the head 6.

An arm 17 secured to the staple case I is used to mount a stationary handle 18 and a movable handle 19 with a return spring 20. The movable handle 19 is hinged to the arm via an axis 21.

At the end 22 of the case I is a projection 23 with an opening 24. A pin 26 is secured to a lateral wall 25 of the projection 23.

A thread is cut at the front end 3 and shank 27 of the supporting rod 2.

The supporting rod 2 is provided with a longitudinal groove 28 made in between the front end 3 and the staple case I.

The plunger 4 comprises essentially a hollow cylinder 29 divided into a number of flaps 30 and secured to the end of a hollow rod 31. The other end of the hollow rod 31 is fashioned into a fork 32 which is adapted to engage the plunger 4 with an end 33 of the movable handle 19.

The hollow cylinder 29 of the plunger 4 is used to install a cylindrical hollow knife 5 with a shaprened edge 34.

The plunger 4 is arranged coaxially within the tubular staple case I, the supporting rod 2 being disposed within its hollow rod 31.

Figure 2:
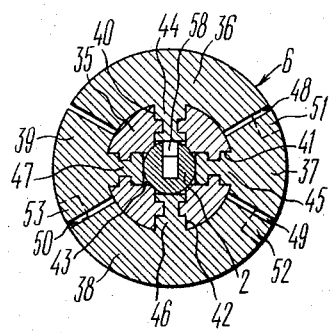
FIG. 2 is a cross sectional view of the surgical suturing instrument for performing anastomoses between structures of the digestive tract taken along line II—II of FIG. 1.

The abutment head 6 is made axially detachable consisting of two members, an internal member 35 and an external member encompassing the internal member 35 and made up of interlockable rests (FIG. 2) (36, 37, 38 and 39).

The abutment head 6 incorporates a means of interlocking the internal member 35 and the rests 36, 37, 38 and 39 of the external member along the surface of their engagement against the radial displacement of the rests 36, 37, 38, and 39 of the external member.

Stapling is effected by means of key grooves 40, 41, 42, and 43 made in the body of the internal member 35 and keys 44, 45, 46 and 47 engaging said grooves 40, 41, 42, and 43, said keys being formed on the rests 36, 37, 38 and 39 of the external member.

The external member is provided with a means for temporary connection of the detachable rests 36, 37, 38 and 39 to form a unified structure.

The rests 36, 37 and 38 are provided with projections 48, 49 and 50 adapted to be received by apertures 51, 52, and 53 of the rests 37, 38 and 39 when the abutment head 6 is mounted on the supporting rod 2.

The longitudinal groove 28 of the supporting rod 2 (FIG. 1) is shaped to accomodate a flat spring 54, one end 55 whereof is rigidly joined to the plunger 4, while its other free end 56 is provided with a tooth 57.

The rest 36 (FIG. 3) of the external member is provided with a mating projection 58 adapted to engage said tooth 57 in such a manner that a mashed pair formed by the tooth 57 and the mating projection 58 permits axial movement of the rests 36, 37, 38 and 39.

The internal member 35 of the abutment head 6 serves to accomodate a nut 59 attached thereto rotatably about its longitudinal axis. The nut 59 is made with a circumferential groove 60 which reciprocates with a tip of the pin 61 securing the nut 59 against displacement along its longitudinal axis. The rests 36, 37, 38 and 39 (FIG. 2) are provided with a circumferential groove 62 (FIG. 3) to receive the knife 5, and with an aperture 63 adapted to accomodate a supporting elastic washer 7.

Figure 4:
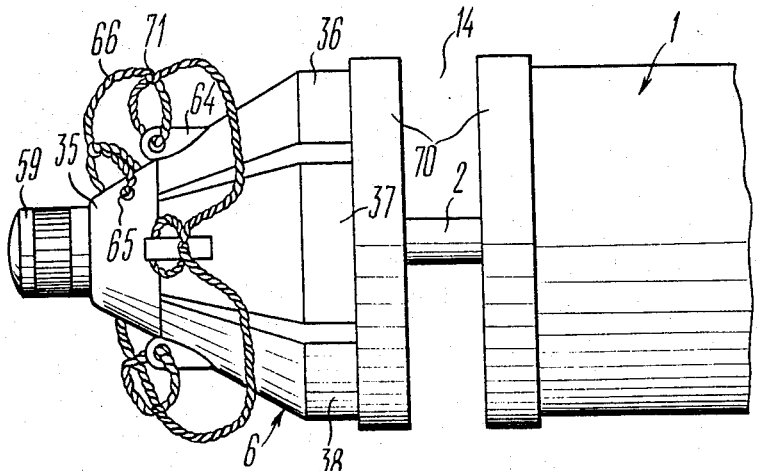
FIG. 4 is a view showing the abutment head of the surgical suturing instrument for performing anastomoses between structures of the digestive tract in the course of performing an anastomosis.

The detachable (FIG. 4) rests 36, 37, 38 and 39 (not shown in FIG. 4) are provided wiith lugs 64, while the internal member is provided with an opening 65 to pass a ligature 66 to maintain the rests 36, 37, 38 and 39 of the external member and the instrument in interlocked position upon dismantling of the abutment head 6.

The grooves 10 (FIG. 1) for bending staples are disposed along the female die 9 describing the outer circumference of the abutment head 6 at a certain pitch so that they make up a circle when viewed in plane.

The staple magazine 8 is arranged coaxially within the tubular staple case I and consists of a series of longitudinal staple grooves 67 disposed along the circumference of the tubular staple case, the number and arrangement of the staples grooves corresponding to the number and arrangement of the grooves 10 for bending the staples made in the abutment head 6. Each of the staple grooves 67 contains a C-shaped metal staple II and a flap 30 of the plunger 4. Hence, the number and arrangement of the flaps 30 of the plunger 4 corresponds to the number and arrangement of the staple grooves 67 and, consequently, to the number and arrangement of the grooves 10 for bending staples.

The drive 12 imparting motion to the plunger 4 comprises essentially a movable handle 19 hinged to the arm 17 of the staple case I, said handle's end 33 being in mash with the fork 32 of the hollow rod 31 of the plunger 4.

The means 13 of adjusting gap 14 between the end 15 of the case I and the end 16 of the abutment head 6 is a nut 68 attached to the case I rotatably about said nut's longitudinal axis.

The nut 68 is connected threadedly to the shank 27 of the supporting rod 2.

The nut 68 is provided with a circular groove 69 adapted to receive the end of the pin 26 which secures the nut against displacement along its longitudinal axis.

The instrument (FIG. 1, FIG. 2 and FIG. 4) is provided with elastic compression rings 70 mounted on the end surface 15 of the staple case I and on the end surface 16 of the abutment head 6 lying in opposition to each other. Viewed in cross section the compression rings 70 have the shape of "C" which affords secure position on the case I and head 6.

The instrument is operated in the following manner.
Preparation for use:

Each staple groove 67 is fitted with a "C"-shaped metal staple using a special forceps so that the sharpened shanks of the staple face toward the female die 9.

The rest 36 is placed over the internal member 35 of the abutment head 6 in such a way that the key 44 (FIG. 2) fits into a key groove 40. The rest 36 is moved in the general direction of the nut 68 (FIG. I) as far as it will go. The rest 37 is then placed so that the key 45 fits into the key groove 40 whereupon the rest is advanced through its full range in the direction of the nut 68 (FIG. 1), the rest 37 eventually abutting against the projection 48 of the rest 36.

Next, the rest 38 is placed so that the key 46 fits into the key groove 42 (FIG. 2) following which the rest 38 is advanced in the direction of the nut 68 (FIG. 1) until it abuts against the projection 49 of the rest 37.

Then, the rest 39 is placed so that the key 47 fits into the key groove 43 (FIG. 2) followed by advancement of the rest 39 through the entirety of its range in the general direction of the nut 68 (FIG. 1) which results in said rest abutting against the projection 50 of the rest 38.

The supporting washer 7 is inserted into the aperture 63 of the abutment head 6.

The edges of the tubular staple case I and of the abutment head 6 are fitted with compression rings 70.

The abutment head 6 is positioned onto the front end 3 of the supporting rod 2 and then secured in position by means of the nut 59 being rotated clockwise. Openings in the lugs 64 (FIG. 3) and the opening 65 in the internal member 35 are used to pass a ligature with a knot 71 tied superiorly adjacent each opening in such a manner that all the rests 36, 37, 38 and 39 are joined to the instrument by the ligature.

Thus assembled, the instrument is subjected to sterilization.

Operation:

The instrument (FIGS. 1 and 3) is introduced into a hollow body structure, for example, the rectum via the anus.

By rotating the nut 68 counterclockwise the supporting rod 2 is advanced along the case I whereby the abutment head 6 is moved away from the case I.

A purse-string suture is placed at one end of the hollow structure (72) (FIG. 3) and then tied around the supporting rod 2.

Rotation of the nut 68 (FIG. 1) counterclockwise causes the abutment head 6 to approximate to the case I to form the suturing gap 14 (the gap between the end 15 of the case I and the end 14 of the abutment head 6).

Next, the movable handle 19 is pressed urging it to rotate about the axis 21 and transmit motion with its end 33 to the fork 32 of the rod 31 whereby the plunger 4 with the knife 5 and the flat spring 54 are extended in the direction of the abutment head 6.

Figure 3:
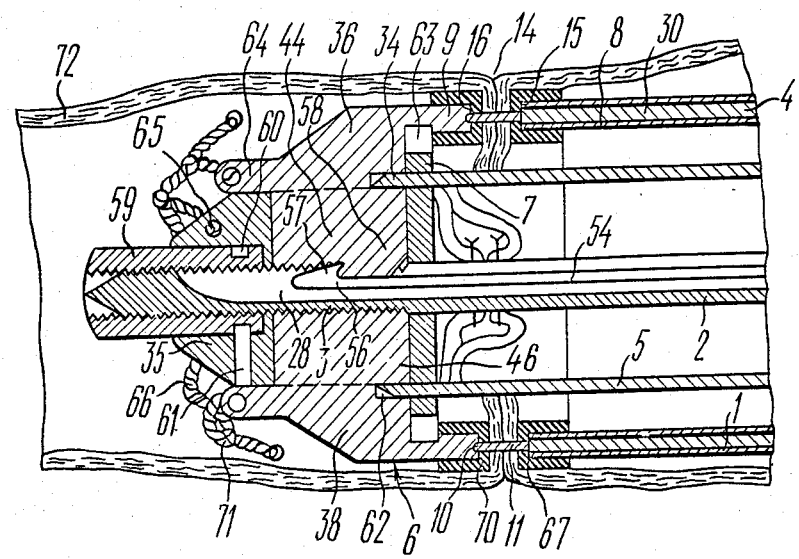
FIG. 3 is an enlarged view of the abutment head of the surgical suturing instrument for performing anastomoses between structures of the digestive tract prior to anastomosing.

During this maneuver the flaps 30 of the plunger 4 push the staples II out of the staple grooves 67 (FIG. 3). The staples, after piercing the compression rings and tissue to be sutured with their sharpened shanks, stop against the staple bending grooves 10 of the female die II and are bent in the shape of "B" securely joining the tissue to the compression rings.

At the same time the knife 5 with its sharpened edge 34 presses the tissue against the supporting elastic washer 7 penetrating into it and excising a circular opening in the tissue.

At this stage the flat spring 54 with its tooth 57 (FIG. 3) engages the projection 58 of the rest 36.

Rotation of the nut 68 causes the abutment head 6 to move away from the case I, but since the rest 36 is in engagement with the flat spring 54 via the mating projection 58 its position remains unchanged, while the internal member 35 of the abutment head 6 is moved away from the case I.

Conjointly with the rest 36, the rests 37, 38 and 39 also remain immobile being in engagement with the internalmember 35 by means of the projections 48, 49 and 50 (FIG. 2) until the keys 44, 45, 46, and 47 are disengaged from the key grooves 40, 41, 42 and 43.

As soon as the keys disengage from the key grooves of the internal member, the rests 36, 37, 38 and 39 become separated to be strung on the ligature 66 as a "garland" attached to the instrument by means of ligature. Such a garland is easily removed through a small opening previously excised with the knife without damaging the anastomosis.

The design of the instrument allows a detachable head of any diameter which can, therefore, be removed through any small opening upon completion of the anastomosis thereby avoiding additional trauma of the tubular structure.

All of this is conducive to reducing the postoperative suture incompetence and consequent mortality.

While only preferred embodiments of the invention have been described above, it will be understood, that various modifications, changes and adaptations will suggest themselves to those skilled in the art without departing from the spirit and scope of the appended claims.

We claim:

1. A surgical suturing instrument for performing anastomoses between structures of the digestive tract comprising a tubular staple case with a supporting rod passing through said tubular case and extending outwardly therefrom with its front end, a plunger with a knife arranged coaxially within the tubular case mounted on said rod movably with respect to its front end, an abutment head mounted on the front end of said rod, said head being made detachable in the general axial direction of said rod and consisting of two members, an internal member detachably mounted on the front end of the rod, and an external member encompassing the internal member and made up of interlockable rests, a means of interlocking the rests and the internal member along the surface of their engagement against the radial displacement of the rests of the external member, said head being provided with a supporting washer for the knife, a staple magazine arranged coaxially within the tubular case, a female die with grooves for bending staples, said female die being mounted on said head, and a drive imparting motion to the plunger with the knife, as well as a means for adjusting the gap between an end of the case and an end of the head.

2. An instrument as set forth in claim 1, wherein stapling is effected by means of key grooves made in the body of the internal member and keys engaging said grooves, said keys being formed on the rests of the external member.

3. An instrument as set forth in claim 1, wherein the supporting rod is provided with a longitudinal groove made in between the front end and the staple case, said groove adapted to accomodate a flat spring, one end whereof is rigidly joined to the plunger, while its other free end is provided with a tooth, and one of the rests or the external member is provided with a mating projection adapted to engage said tooth in such a manner that a meshed pair formed by the tooth and the mating projection permits axial movement of the rests.

4. An instrument as set forth in claim 3, wherein a tenon and mortise means is provided for temporary connection of the interlockable rests.

5. An instrument as set forth in claim 1, wherein the interlockable rests are provided with lugs, and the internal member is provided with an opening for passing a ligature to maintain the rests of the external member attached to the instrument in interlocked position upon dismantling of the abutment head.

6. An instrument as set forth in claim 1, wherein the end surface of the staple case and the end surface of the head lying mutually in opposition are used to loosely mount a compression ring.

* * * * *